(12) United States Patent
Mimura et al.

(10) Patent No.: US 6,261,521 B1
(45) Date of Patent: *Jul. 17, 2001

(54) SAMPLE ANALYSIS SYSTEM AND A METHOD FOR OPERATING THE SAME

(75) Inventors: Tomonori Mimura, Tomobe-machi; Ryuichiro Kodama, Hitachinaka; Atsushi Takahashi; Hiroshi Mitsumaki, both of Mito, all of (JP)

(73) Assignee: Hitachi, Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/055,713

(22) Filed: Apr. 7, 1998

(30) Foreign Application Priority Data

Apr. 9, 1997 (JP) .................................................. 9-090761

(51) Int. Cl.[7] ..................................................... G01N 35/02
(52) U.S. Cl. ............................... 422/67; 422/63; 422/65; 436/43; 436/47; 436/48; 436/50; 700/266
(58) Field of Search ....................... 422/63, 65, 67; 436/43, 47, 48, 50; 364/528.01; 700/266

(56) References Cited

U.S. PATENT DOCUMENTS

| 5,087,423 | * | 2/1992 | Ishibashi | 422/67 |
| 5,207,986 | * | 5/1993 | Kadota et al. | 422/65 |
| 5,209,903 | * | 5/1993 | Kanamori et al. | 422/65 |
| 5,260,868 | | 11/1993 | Gupta et al. | . |
| 5,380,488 | * | 1/1995 | Wakatake | 422/65 |
| 5,614,415 | * | 3/1997 | Markin | 436/48 |
| 5,623,415 | * | 4/1997 | O'Bryan et al. | 346/478.13 |
| 5,730,939 | * | 3/1998 | Kurumada et al. | 422/67 |
| 5,876,670 | * | 3/1999 | Mitsumaki et al. | 422/65 |
| 5,902,549 | * | 5/1999 | Mimura et al. | 422/65 |

FOREIGN PATENT DOCUMENTS

| 795754 | 9/1997 | (EP) . |
| 7-092171 | 4/1995 | (JP) . |
| 7-92171 | 4/1995 | (JP) . |
| WO94/02857 | 2/1994 | (WO) . |

* cited by examiner

Primary Examiner—Jill Warden
Assistant Examiner—Kathryn Bex
(74) Attorney, Agent, or Firm—Mattingly, Stanger & Malur (57) ABSTRACT

A system setup for a sample analysis system having a plurality of analysis units placed along a main conveyor line prior to its analysis operation. The system setup includes setup of analysis units in combination with different types of reagent supply units, setup of analysis routes as to whether it is a stationary type or an automatic type, and setup of analysis items for each analysis unit as to which analysis item should be assigned to which analysis unit having which reagent supply type. These settings are executed through monitoring of setup screens displayed on a screen display unit, and the contents of such a setting are stored and registered in a memory of the controller.

3 Claims, 7 Drawing Sheets

FIG. 5(A) AUTOMATIC

FIG. 5(B) STATIONARY

FIG. 5(C) STATIONARY

SAMPLE ANALYSIS SYSTEM AND A METHOD FOR OPERATING THE SAME

BACKGROUND OF THE INVENTION

1. Field of the Invention

The present invention relates to a sample analysis system and a method for operating the same, and in particular, it relates to a sample analysis system set up to allow a sample on a conveyor line to be transferred to at least one of a plurality of analysis units for analysis thereof, and a method for operating the same.

2. Description of the Related Art

Related sample analysis systems have been proposed for analyzing a plurality of analysis items for biological samples such as blood or urine using a plurality of analysis units arranged along a conveyor line which conveys such samples. For example, J-A 7-92171 discloses that a plurality of analysis units, each having a different processing number of samples to be analyzed per unit time, are arranged along a main conveyor line, and that a subline is provided between the main conveyor line and each of the plurality of analysis units.

J-A 7-92171 discloses an analysis system in which information in a bar code labeled on each sample container is read at an inlet of a main conveyor line, then the container being carried on the main conveyor line is transferred to a corresponding subline of one of the plurality of analysis units, and after sample processing, the container is returned from the subline to the main conveyor line. Then, the sequence of transfer of each container is controlled such that a mean time of analysis processing in each analysis unit becomes equal.

The above-mentioned analysis systems of the related art, however, have a problem that when there occurs a change in sample test environments in laboratories, its test efficiency will decrease.

SUMMARY OF THE INVENTION

An object of the invention is to provide a sample analysis system which can change its system configuration for a sample processing function without need of changing arrangements of a plurality of analysis units in the sample analysis system.

Another object of the invention is to provide a sample analysis system which can change a combination of a plurality of analysis items which can be processed therein depending on changes in sample test environments.

A sample analysis system according to the invention includes : a first memory means for storing analysis items to be analyzed for each sample on each sample rack; a screen display means for displaying an analysis item entry screen for each type of reagent supply unit to be used in each analysis unit; a second memory means for storing analysis items information for each analysis unit having been entered through the screen display unit; a determination means for determining for each sample rack, on the basis of its analysis items information stored in the first memory means, to stopover at which analysis unit of the plurality of analysis units according to data stored in the second memory means; and a control means for controlling operations of conveyor and transfer lines such that the sample rack is transferred to a designated analysis unit.

In this sample analysis system, its reagent supply types include two types, namely, a pipetter reagent supply type and a dispenser reagent supply type. Further, this sample analysis system is provided with a third memory means for storing information on a combination of analysis units having been set up preferably through the screen display means. This screen display means displays, on its screen for setting up a combination of the plurality of analysis units, positions of installation of respective analysis units and their reagent supply types.

A method of configuration for the sample analysis system of the invention includes the steps of displaying a screen having an analysis item setup block for setting up analysis items corresponding to its reagent supply type of each analysis unit on the display; and storing in the memory the combination of the plurality of analysis units which have been assigned with analysis items.

Further, the method of operating the sample analysis system according to the invention includes the steps of displaying a screen having an analysis unit setup button and an analysis item setup button on a display in response to an instruction to display a system setup screen; displaying a screen on the display for setting up a combination of a plurality of analysis units to be used upon selection of the analysis unit setup button; displaying a screen having a reagent supply type indication block and an analysis items setup block on the display corresponding to each analysis unit upon selection of the analysis item setup button on the system setup screen; storing the combination of the plurality of analysis units having been set up and their analysis items having been set up for each analysis unit in the memory means; and changing a destination of the sample rack containing samples on the conveyor line to stopover between the plurality of analysis units in accordance with analysis items of the sample to be analyzed.

In a preferred embodiment of the invention, analysis items information of each sample on the sample rack to be delivered to the conveyor line is read by an ID information reader before the sample rack is conveyed by the conveyor line, and in the analysis unit which is destined to stop over for the sample rack which contains the sample, the analysis items information of which has been read, a sampling operation of the sample for its analysis is executed. Further, when an analysis item display instruction occurs after the analysis items for each analysis unit have been set, a table indicating analysis items, the processing of which can be shared by plural analysis units having been set up, is displayed corresponding to each analysis unit on the display.

BRIEF DESCRIPTION OF THE DRAWINGS

The invention and its other features and advantages will be more clearly understood in the following description with reference to the accompanying drawings, in which.

DESCRIPTION OF THE PREFERRED EMBODIMENT

A preferred embodiment of the invention will be described with reference to FIGS. 1–4.

Figure 1:
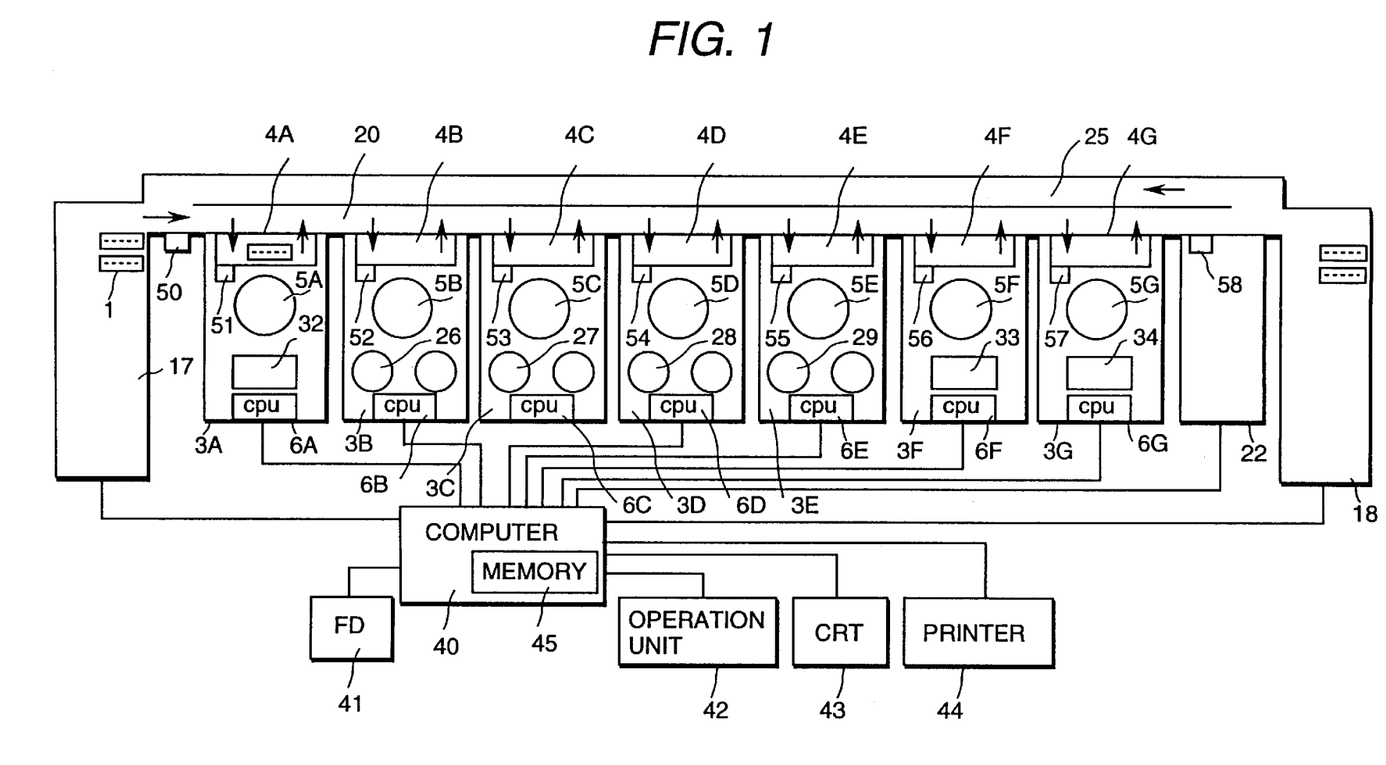
FIG. 1 is a schematic block diagram of a system configuration of a sample analysis system according to one embodiment of the invention.
Figure 2:
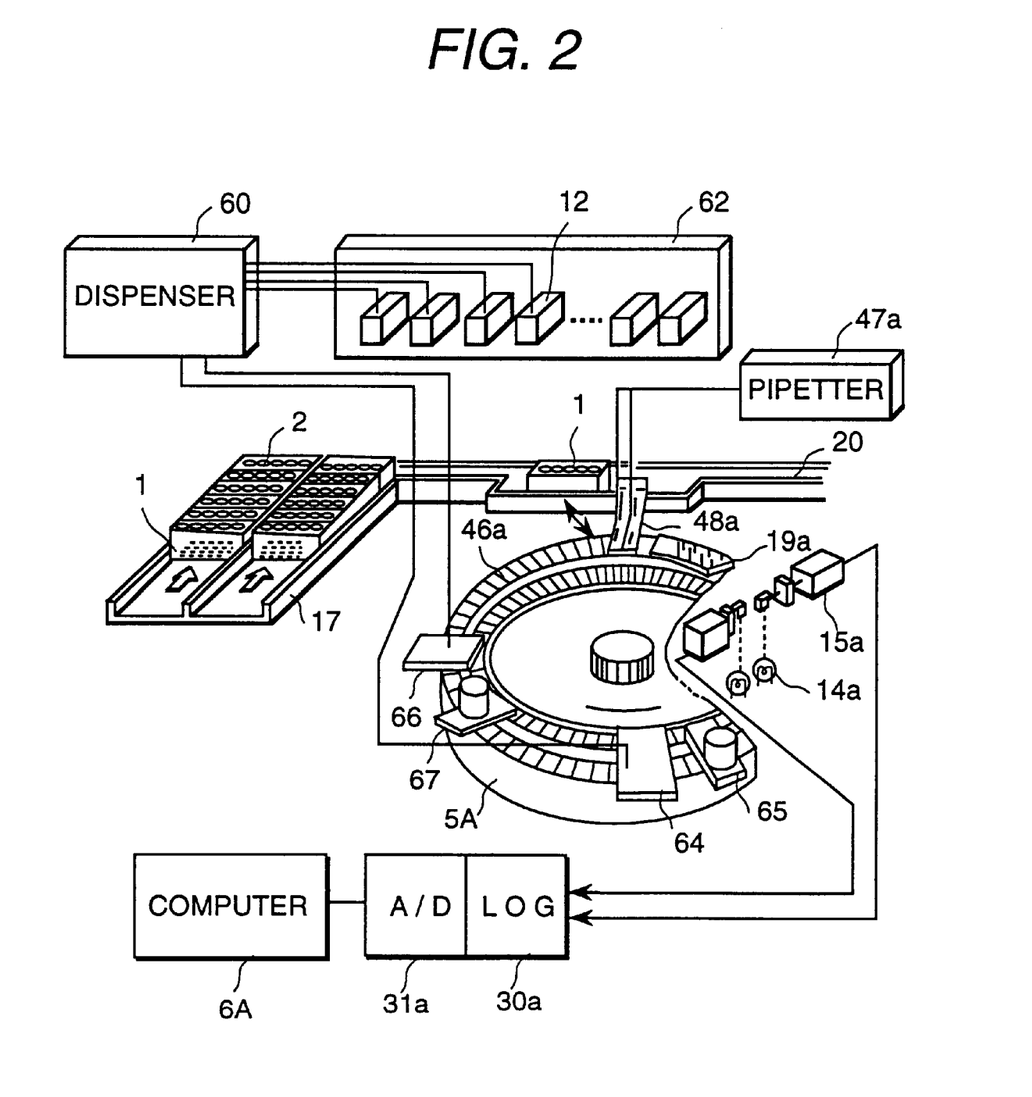
FIG. 2 is a schematic diagram indicating a structure and its operation of an analysis unit having a dispenser type reagent supply function in the embodiment of FIG. 1.
Figure 3:
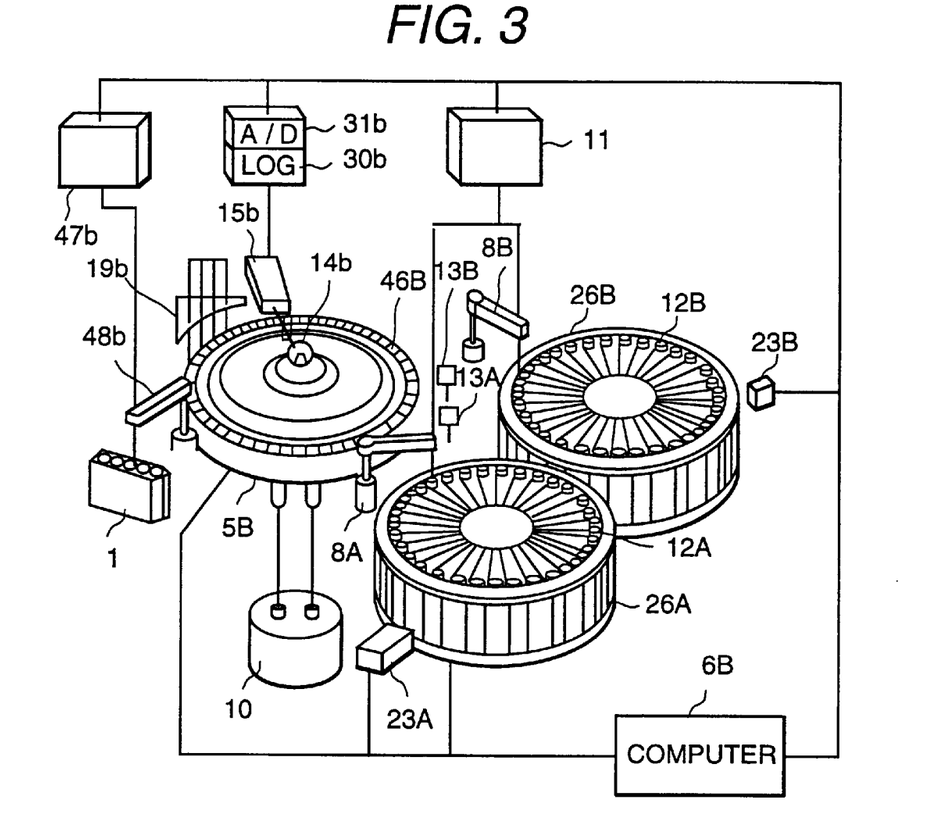
FIG. 3 is a schematic diagram indicating a structure and its operation of an analysis unit having a pipetter type reagent supply function in the embodiment of FIG. 1.

A sample analysis system of FIG. 1 includes analysis units of a dispenser type as indicated in FIG. 2 and of a pipetter type as indicated in FIG. 3 in combination. Analysis units 3A, 3F and 3G of FIG. 1 are dispenser type analysis units having fixed analysis channels and dedicated pipette nozzles for each of a plurality of reagents. Analysis units 3B, 3C, 3D and 3E are a pipetter type analysis unit in which analysis channels are not fixed thereby allowing random access, and a single reagent pipette nozzle is allowed to pipette appropriate reagents sequentially according to designated analysis items.

The sample analysis system embodying the invention of FIG. 1 is indicated to use blood serum as its sample species, however, it is not limited thereto, and this system can be arranged such that, for example, analysis units 3A, 3B and 3C analyze blood serum, analysis units 3D and 3E analyze blood plasma, and analysis units 3F and 3G analyze urine.

In FIG. 1, analysis units 3A to 3G are provided with sample lines 4A to 4G, respectively, each of which is a dedicated line which has a function to fetch sample rack 1 which is a holder of sample containers from main conveyor line 20, to move the rack to a sampling position, then to return it to the main conveyor line 20. Further, each analysis unit is installed corresponding to each sampling line 4A–4G, and is provided with an ID information reader 51–57 which reads out ID information of sample rack 1 or ID information of each sample container carried by sample rack 1; a reaction portion 5A–5G in which a reaction proceeds as specified in accordance with analysis items between the samples and reagents, and the result of reactions is optically measured; and reagent supply sections 26–29, 32–34. Numerals 26, 27, 28 and 29 of respective analysis units depict pipetter type reagent supply devices, and numerals 32, 33 and 34 depict dispenser type reagent supply devices.

A rack supply portion 17 has an area sufficient to be able to set a plurality of sample racks 1 therein, and a delivery mechanism to deliver the plurality of sample racks 1 one by one to main conveyor line 20. A rack recovery portion 18 has an area to recover sample racks 1 which hold sample containers which have been sampled for analysis processing in at least one of the plurality of analysis units, and an alignment mechanism to align the recovered sample racks in order. A temporary storage portion 22 stores each sample rack 1 having been sampled at least in one of the plurality of analysis units temporarily until the result of measurements of its samples is output, sends it back for reexamination via return conveyor line 25 of main conveyor line 20 when it is required, and conveys the sample rack to rack recovery unit 18 when no reexamination is required.

A control unit has a host control computer 40, distributed control computers 6A–6G provided in respective analysis units for executing required processing and control therefor, and a floppy disk memory 41. Data processing of output signals from a photometer provided in each analysis unit is shared and executed by the analysis unit computers 6G, and host control computer 40 connected thereto executes operation control of each analysis portion, the rack transfer system and other necessary portions in the system, and also executes arithmetic operations and control required for various information processing. Load sharing by computers, however, is not limited to the above, and can be modified to have various modes thereof according to necessity of architecture, or the distributed computers at each analysis unit can be eliminated by using only the host control computer 40. The host control computer 40 is provided with a memory portion 45, and is connected to an operation unit 42 for data entry, a CRT 43 for information display and a printer 44 for output of the result of measurements.

A sample rack 1 is a holder having a box-like shape as depicted in FIG. 2 in which a plurality of sample containers 2, for example, five in number, are loaded, respectively. However, the sample rack shape is not limited to a box, and any shape may be adopted. On an external surface of sample rack 1, an ID information record medium indicative of rack ID information is attached. On an external surface of each sample container 2, an ID information record medium indicative of its sample ID information is attached. As the ID information record medium, a bar-code label, magnetic recording medium and the like are used. A bar-code attached on sample rack 1 has information regarding its rack serial number and sample species. A bar-code attached on each sample container 2 has information regarding its sample, for example, serial number, date of entry, name and entry number of patient, sample species, analysis items requested and the like.

ID information reader 50 shown in FIG. 1 reads ID information (on bar code) of sample rack 1 and sample container 2 before it is delivered by main conveyor line 20, and inputs its result to computer 40. Further, ID information reader 58 provided in temporary storage section 22 reads ID information from the bar-code on sample rack 1 or sample container 2 when they enter and exit from temporary storage section 22, and transmits its data to host computer 40.

Reagent bottles 12A, 12B for use in various items of analysis which are accommodated in a reagent supply section in each analysis unit 3A–3G have their reagent ID information on bar code or the like attached on their external surfaces. This reagent ID information includes reagent manufacture lot number, reagent bottle size, quantity of reagent that can be serviced, expiration date, sequential number which differs from bottle to bottle, analysis items and the like. Such reagent ID information is read by the bar code reader, and entered into memory section 45 corresponding to the set position of its reagent bottle, in the reagent supply unit, allowable number of analysis remaining calculated from the initial quantity of solution and a unit dose, types of analysis items, serial number of the analysis unit accommodating the reagent, and the like.

Main conveyor line 20 which includes a conveyor belt for carrying sample racks 1 and a motor for driving the belt is controlled by the control unit to transport the sample racks continuously to a desired position. Each sampling line 4A–4G can move its conveyor belt intermittently so as to receive a sample rack at a rack entry position, stop it at a sampling position and at a rack exit position. Each sample rack 1 delivered by main conveyor line 20 is moved along a row of analysis units, stopped in front of a particular analysis unit designated by the control unit, and immediately transferred to a rack receive position on the sampling line of the designated analysis unit by its rack transfer mechanism which will be described in greater detail later. A sample rack 1 having completed sample pipetting operation at its sampling position is returned from the rack exit position on the sampling line to main conveyor line 20 by the rack transfer mechanism.

With reference to FIG. 2, an example of a configuration of an analysis unit having a dispenser type reagent supply unit will be described. Reactor section 5A in analysis unit 3A is comprised of concentrically aligned two rows of reactors, each row including a plurality of transparent reactors 46a, and a multi-wavelength photometer 15a provided for each row of reactors for analyzing spectroscopic multiwaves of light emitted from light source 14a and transmitted through reactor 46a. To serve each row of reactors, there are disposed in the vicinity of reactor section 5A a sample pipetter 48a having a pipette nozzle connected to sample pipetter pump 47a; a first reagent nozzle group holder portion 64 and a second reagent nozzle group holder portion 66, each connected to reagent dispenser pump 60; a first stirrer 65 and a second stirrer 67; and a reactor cleaning mechanism 19a. A reagent refrigerator 62 stores therein reagent bottles 12 of a first reagent and a second reagent for use in a plurality of analysis items (only for required analysis items), which are aligned therein and cooled at a predetermined low temperature. Each reagent solution in each reagent bottle is supplied via each tube and by reagent dispenser pump 60 to a corresponding reagent injection nozzle disposed over the rows of reactors. In this case, dispenser type reagent supply section 32 in analysis unit 3A of FIG. 2 includes reagent dispenser pump 60 of FIG. 2, reagent refrigerator 62 which cools the plurality of reagent bottles 12 therein, the first reagent nozzle group holder 64, the second reagent nozzle group holder 66 and the like.

Each sample rack 1 supplied from rack supply unit 17 is conveyed by main conveyor line 20, and when any analysis by analysis unit 3A is required, sample rack 1 is transferred to sampling line 4A corresponding to the analysis unit 3A. A predetermined amount of a sample is aspirated using a pipette nozzle of sample pipetter 48a from the sample container on sample rack 1 positioned at its sampling position and is injected into reactor 46a. Into this reactor positioned at a predetermined position on the reactor rows, a reagent corresponding to a specified analysis item is injected to produce a reaction. After a predetermined period of time, a reaction solution in reactor 46a is subjected to measurement of its optical property using multi wavelength photometer 15a. An output signal from multi wavelength photometer 15a is processed by logarithm converter 30a and A/D converter 31a under control of distributed computer 6A of the analysis unit, then it is transmitted to host control computer 40. Dispenser type analysis units 3F and 3G have the same configuration as that of analysis unit 3A.

Now, with reference to FIG. 3, an example of a configuration of an analysis unit having a pipette type reagent supply unit will be described. Within reactors 46b disposed in array on reactor section 5B in analysis unit 3B, reactions are allowed to proceed between samples and reagents specified for particular analysis items. Sample rack 1 transferred from main conveyor line 20 to sampling line 4B (indicated in FIG. 1) is positioned at its sampling position thereon, where using a pipette nozzle of sample pipetter 48b, the sample is aspirated and a predetermined quantity of the sample is injected into reactor 46b. Sample pipetter 48b is provided with sample pipetter pump 47b. Reactor section 5B is kept at a constant temperature (for example, at 37° C.) by isothermal liquid supplied from an isothermal tank 10.

Pipetter type reagent supply unit 26 in FIG. 3 is provided with two reagent disks 26A and 26B for use of a first reagent and a second reagent. A plurality of reagent bottles 12A and 12B containing various reagents prepared for a number of analysis items have their reagent ID information indicated on bar code attached on their external walls, respectively. After reagent bottles 12A and 12B are loaded on reagent disks 26A and 26B, reagent ID information of each reagent bottle is read by bar code readers 23A and 23B. The information having been read out is associated with the set position of its reagent bottle on the reagent disk, its corresponding analysis item, the analysis unit number to which its reagent bottle is set, and the like, then is entered into memory 45. Reagent pipetters 8A and 8B each having a pipetter nozzle which is free to swivel and movable vertically are connected to reagent pipette pump 11.

The array of reactors 46b having been injected with samples is rotated. A predetermined amount of reagent is aspirated using reagent pipetter 8A from reagent bottle 12A which contains the first reagent and which is positioned at a reagent aspiration position corresponding to its analysis item, then its first reagent is injected into reactor 46b which is positioned at a reagent adding position. After their contents are stirred by stirrer 13A at a stirring position, the array of reactors is moved several times, then when reactor 46b arrives at a second reagent adding position, reagent pipetter 8B aspirates a reagent from reagent bottle 12B which is positioned at its reagent aspiration position corresponding to its analysis item and injects the aspirated reagent into the reactor. Then, the contents of the reactor are stirred by stirrer 13B. With rotation of the array of reactors, a light flux from light source 14b is admitted to pass through reactor 46b, and the light having passed through the reaction solution in reactor 46b is examined by multi wavelength photometer 15b. Output signals of wavelength corresponding to any designated analysis items are processed by logarithm converter 30b and A/D converter 31b which are controlled by analysis unit computer 6B, and digital signals obtained are transmitted to host control computer 40. Reactor 46b having completed its measurements is cleaned by cleaning mechanism 19b and is used for subsequent tests. Configurations of analysis units 3C, 3D and 3E are the same as that of analysis unit 3B.

Sample analysis operation in the sample analysis system of FIG. 1 will be described in the following.

It is assumed in the sample analysis system of FIG. 1 that before a sample rack 1 is set in rack supply unit 17, a combination of analysis units to be used therein and kinds of analysis items that can be analyzed in each analysis unit to be used have been preset. This system setting will be described later.

Before starting analysis operation of samples, an initial setup screen for setting up analysis conditions is displayed on a display device which is CRT 43. Then, various analysis conditions are entered to be set up by key operation of operation unit 42 and through the screen of CRT 43. Analysis items designated to be tested by the requester for each sample are entered, together with the same serial number or client's number labeled on its sample container, into host control computer 40 through operation unit 42. In this case, memory means 45 of computer 40 functions as the first memory means which stores the analysis items of each sample designated to be analyzed.

Further, information on analysis conditions designated for each analysis item is stored in floppy disk memory 41. Among these analysis conditions, analysis item code consists of five digit numbers. Parameters of the analysis conditions to be used commonly between plural analysis units designated for the same analysis items include measurement wavelength in the photometer, sample pipetting quantity, calibration curve correction method, reference solution concentration, the number of bottles of reference solution, limit value for analysis value abnormality check, and the like. Parameters of the analysis conditions which are stored corresponding to each reagent bottle include the number of required reagents, for example, from the first to the fourth reagents, codes of reagent bottles consisting of 5 digit numbers, pipetting quantity of reagents, the number of tests available per bottle of reagents, and the like. Analysis conditions of analysis units 3A, 3B and 3C are set to accept blood serum samples, analysis units 3D and 3E to accept blood plasma samples, and analysis units 3F and 3G to accept urine samples, respectively. Acceptable sample species and their analysis unit numbers are registered in the host control computer.

Upon loading of reagent bottles in each reagent supply unit in respective analysis units 3A–3G, reagent ID information of each reagent bottle is registered in host control computer 40 associated with its corresponding analysis unit serial number. In this case, assume, for example, that a group including analysis units 3A, 3B, 3C and 3G is set up as a group assigned to carry out blood serum testing. For analysis units 3A and 3G among the group, their reagent supply units 32 and 34 are loaded, for example, with reagent bottles containing GOT and GPT which are hepatoscopy test items which have many sample test requests, and bottles containing calcium, UA and BUN for emergency test items. Reagent supply section 26 of analysis unit 3B is loaded, for example, with reagent bottles containing GOT, GPT which are hepatoscopy test items, and other reagent bottles containing reagents for other analysis items, the number of requests for which is not many. Then, reagent supply section 27 of analysis unit 3C is loaded with reagent bottles containing, for example, calcium, UA, BUN which are emergency test items, and other reagents for other analysis items, the number of request for which is not many. Therefore, hepatoscopy test items can be examined by the three analysis units of 3A, 3B and 3G while emergency test items can be analyzed by three analysis units of 3A, 3C and 3G. What reagent for what analysis item is to be loaded in duplicate in which analysis unit is determined by the operator in consideration of actual conditions of laboratories in respective facilities.

When respective reagent bottles, 12, 12A, 12B are loaded in each reagent supply section, each reagent ID information thereof attached on each reagent bottle is read and then using each reagent bottle code as a key, the information having been entered as its analysis conditions parameters is retrieved. Then respective data corresponding to this reagent bottle such as its analysis item, size of the bottle, the number of analysis tests available, set position of the reagent bottle and the like are associated with each other and entered into host control computer 40. At the same time, a maximum allowable number of analyses for the same sample species and for the same analysis item calculated on the basis of a total number of reagent bottles for the same analysis item loaded in the plurality of analysis units which allow analysis of the same species and the same analysis item is registered, and displayed on CRT 43 as required.

After respective reagents corresponding to respective analysis items required for each analysis unit have been loaded, prior to subjecting samples to analysis processing, calibration curve correction operation for each analysis unit is carried out for all analysis items which can be analyzed in each analysis unit. Since a calibration curve correction value differs depending on a difference of reagent bottles set in each analysis unit, results of calibration curve corrections obtained in each analysis unit for each analysis item is stored in memory 45 of host control computer 40. These results of correction are used in calculation of concentrations when any analysis item corresponding thereto is being analyzed in each analysis unit.

At the same time when one of the plurality of sample racks 1 placed on rack supply unit 17 is pushed forward to main conveyor line 20, ID information of sample rack 1 and sample container 2 is read by ID information reader 50. On the basis of the information having been read, the group including analysis units 3A, 3B, 3C and 3G assigned for blood serum testing is selected. Otherwise, as a group of analysis units in a state to be used, analysis units 3A, 3B, 3C and 3G are recognized.

Further, upon reading of the sample ID information, the registration status of its sample number such as serial number, and analysis items are collated, and each analysis item designated to be tested for each sample on sample rack 1 is identified, then it is determined by host control computer 40 which one of analysis units 3A, 3B, 3C and 3G should proceed with which analysis items for the sample having been identified. In this case, host control computer 40 monitors the serial number of analysis items having been designated for each analysis unit to carry out and how long it will take until completion of its sampling. In particular, with respect to any particular analysis items which can be analyzed by a plurality of analysis units, it is judged which analysis unit is best to be assigned with that analysis item in order to be most efficient. For example, with respect to GOT and GPT of particularly designated analysis items, it is judged that either of analysis units 3A, 3B and 3G have a minimum number of samples in queue to be processed at that time, then one of them which has a minimum wait time is designated as its analysis unit. According to a degree of busyness among a plurality of analysis units, a particular analysis unit is automatically designated to proceed with a particular analysis item designated. However, it is not limited to such automatic designation method, and it is possible also for the operator to enter any priority of use for respective analysis units for each analysis item via operation unit 42 in advance.

A sample rack 1 holding samples which have a plurality of analysis items to be tested and its destination having been determined (for example, destined to analysis unit 3B) is conveyed to its destined analysis unit 3B by main conveyor line 20, and is stopped in front of the entrance to sampling line 4B of analysis unit 3B. Then, the sample rack 1 is transferred to sampling line 4B and moved to its sampling position, where a predetermined sample is aspirated by sample pipetter 48b to be injected into reactor 5B. Then the sample rack is returned to main conveyor line 20.

When there remains any analysis items to be tested for the sample on sample rack 1, sample rack 1 is conveyed further to analysis unit 3C by main conveyor line 20, transferred to sampling line 4C, and subjected to sample pipetting.

Amounts of reagents remaining in respective reagent bottles for use in testing of respective analysis items in each analysis unit in FIG. 1 are monitored by host control computer 40. As a method for monitoring the remaining amounts of reagents, a level gage attached to the reagent pipette nozzle may be used to detect the level of reagent liquid in the bottle every time the reagent is aspirated, or a subtraction method may be used which subtracts from a total allowable number of analysis tests every time of reagent pipetting. In the case of any of these methods, whether or not the amount of any reagent for use in the analysis of that particular analysis item runs short is decided by host control computer 40 which determines whether or not the remaining number of allowed tests of analysis has reached a predetermined value. The predetermined value in this case is set at a small number such as 0, 1, 2 or the like which indicates a remaining number of tests. Further, when, for example, GOT reagent in designated analysis unit 3B is judged to be in shortage, GOT analysis in analysis unit 3B is interrupted and a simultaneous switchover of GOT analysis processing to analysis unit 3A which has a plenty of GOT reagent remaining therein is enabled. Thereby, subsequent samples requiring GOT analysis are transferred to analysis unit 3A which is in the second priority order in the group of processing GOT analysis.

The control unit in the embodiment of FIG. 1 apprehends which of respective analysis items is designated to which analysis unit to carry out its analysis processing, and these data are stored in memory 45. Host control computer 40 stores information regarding which of respective analysis items is being processed by which analysis unit in its memory table, and displays the information edited in table on CRT 43 when requested from the operator.

In the apparatus of the embodiment of FIG. 1, the operator can instruct each of analysis units 3A–3G to start or stop its operation through keying via operation unit 42. On the basis of instructions from the operator unit, host control computer 40 controls such that a sample rack 1 delivered from rack supply unit 17 is transported by main conveyor line 20 to either one of appropriate analysis units other than the analysis unit which has been interrupted of its operation. In particular, in the time zone such as night shift time when samples need to be analyzed in emergency but its frequency is not great, the overall system can be operated in such a manner, for example, that only analysis units 3C and 3G for blood serum testing are kept operating and all other analysis units are stopped in their operation. In the time zone when the number of samples increases, other analysis units will resume their operation.

Still further, in the system arrangement of the embodiment of FIG. 1, if an abnormality arises in any of the analysis units causing it to be unable to continue its analysis operation, the control unit instructs another analysis unit to take over its analysis assignment and its sample rack to be delivered thereto. For example, by providing a plurality of reagents for use for a plurality of analysis items in duplicate in two analysis units 3B and 3C, analysis operation for the plurality of analysis items can be ensured to be continued without interruption.

Figure 4:
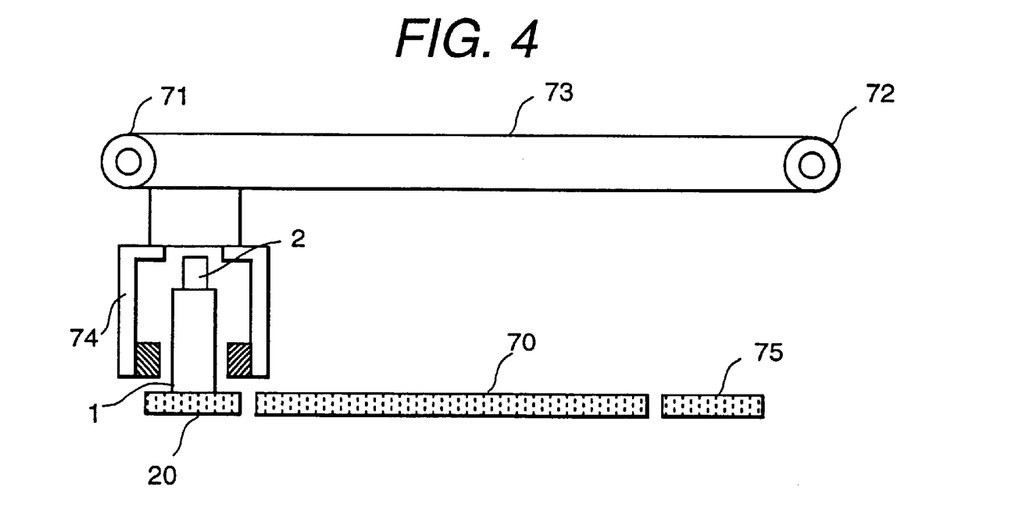
FIG. 4 is a schematic diagram indicating a rack transfer mechanism in the embodiment of FIG. 1.

Now, with reference to FIG. 4, an example of a rack transfer mechanism of the invention is depicted. As such rack transfer mechanism, a traveling robot provided with a rack grip arm, a mechanism having a shove lever to shove a sample rack between the main conveyor line and the sampling line, and the like may be used. The example of FIG. 4 depicts one with a rack grip arm.

A communicating path 70 with a sufficient width to allow passage of a sample rack 1 is provided between main conveyor line 20 and sampling line 75 (4A–4G in FIG. 1) on each analysis unit. The rack transfer mechanism is provided in the upper portion of communicating path 70, which includes primary pulley 71 attached to a motor drive axis, idler pulley 72, belt 73 wound around these pulleys, and gripper 74 having a pair of movable fingers and connected to belt 73. In FIG. 4, all of communicating path 70, sampling line 75, primary pulley 71 attached to the motor drive, idler pulley 72, belt 73 and gripper 74 are provided not on the side of the main conveyor line but on the side of each analysis unit.

FIG. 4 indicates a state of a gripper 74 which is waiting for arrival of a sample rack 1 on the main conveyor line. In this state, gripper 74 grips the sample rack 1 and the gripper is moved via connection path 70 to the position of sampling line 75 by driving the motor, then sample rack 1 is released from the gripper to be placed on sampling line 75. The reverse operation of the above is executed when returning sample rack 1 from sampling line 75 to main conveyor line 20.

The descriptions given hereinabove are concerned with the operation of analysis (examination). In this embodiment of the invention, however, prior to execution of its analysis operation, a system setting is executed. That is, a relationship between analysis units to be used and their positions to be installed, i.e., setting of analysis units as to what type of analysis unit placed at which position should be used, setting of analysis route as to how these analysis units should be combined for use, and setting of analysis items as to what analysis items should be assigned to which analysis unit respectively. Contents of these settings are stored in memory 45 of host control computer 40. Prior to a detailed description of this system setting, a brief description will be given to help understand it more easily in the following.

Figure 5A:
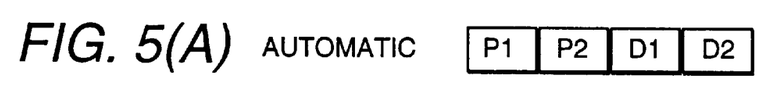
FIGS. 5(A)–(C) show examples of combinations of analysis units.
Figure 5B:
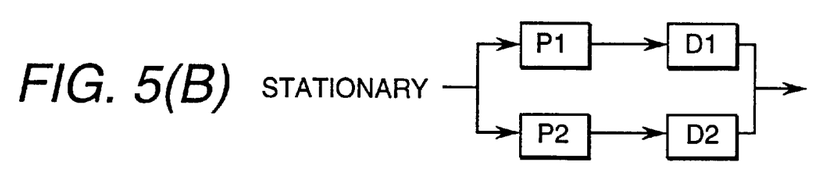
Figure 5C:
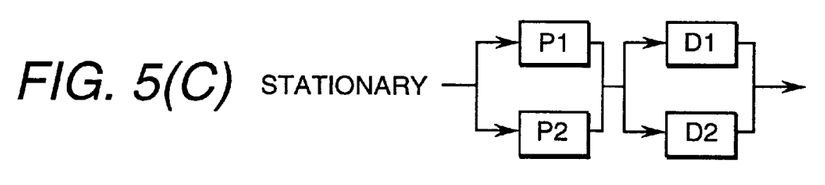

Any number of analysis units may be used, however, if the number is assumed to be n, there is a possibility of a combination of analysis units of n-th power of 2. To make it simple, it is assumed the number of analysis units to be used is four, two of which are analysis units P1 and P2 which use a pipetter type reagent supply method, and the other two of which are analysis units D1 and D2 which use a dispenser type reagent supply method. In this case, P depicts pipetter type, and D depicts dispenser type. To make it easy to understand, it is assumed there are three routes of analysis as roughly indicated in FIGS. 5(A), (B) and (C). FIG. 5(A) depicts a typical analysis route which can be automatically selected and determined by the host control computer in accordance with the analysis items requested for each sample as to which analysis units and in what sequence thereof the sample should stop over. In this respect, the analysis route indicated in FIG. 5(A) will be referred to as an "automatic" analysis route.

FIG. 5(B) depicts a parallel type, in which a combination of analysis units P1 and D1 which are connected in series, and another combination of analysis units P2 and D2 which are connected in series are further connected in parallel. FIG. 5(C) is a hybrid type in which a combination of analysis units P1 and P2 which are connected in parallel, and another combination of analysis units D1 and D2 which are connected in parallel are further connected in series.

Respective analysis items to be analyzed by respective analysis units P1, P2, D1 and D2 are determined by item setting to be described later. However, to make it simple to understand, it is assumed here that respective analysis items which can be analyzed by analysis units P1 and P2 are the same as each other, and further that respective analysis items which can be analyzed by analysis units D1 and D2 are also the same as each other. Then, in FIG. 5(B), a first analysis route formed by analysis units P1 and D1 connected in series and a second analysis route formed by analysis units P2 and D2 connected in series are known to be the same as each other. Namely, there exist two of the same analysis router. According to this idea, in FIG. 5(C), four of the same analysis routes exist.

In either case of FIG. 5(B) or FIG. 5(C), it is determined by the host control computer which analysis route from a plurality of stationary and same analysis routes should be selected for use. Further, determination of its selection is executed according to a predetermined criterion such as whether or not its analysis route is not occupied, whether or not there are remaining adequate reagents, or in the case where all of the analysis routes are available for use, the analysis route having a younger number is selected. In FIG. 5, analysis routes of (B) and (C) are referred to as a stationary analysis route.

Now, as will be described with reference to a flow chart in FIG. 6, a setup of analysis units is executed in step (601). In this step, it is determined and registered as to what analysis units placed at which positions should be utilized. In other words, step (601) is a step for determining and registering which analysis units to be operated for a particular analysis operation are required. Then, in the case of the "stationary" arrangement, it is possible to add a step to determine and register which analysis units and in what sequence thereof the sample rack should stopover during analysis operation, namely, to determine a transfer route of the sample rack.

In step (602), it is designated whether a combination of the plurality of analysis units is "automatic" or "stationary". In the case where its designation is "automatic", respective analysis items that can be analyzed by each analysis unit are set up for each analysis unit in step (603). More particularly, for analysis units P1 and P2 which are set up to execute the same analysis items, for example, analysis items such as CRP, BUN, CRE, GLU and the like are set up using a display screen of FIG. 11, which will be described later. In the same manner, for analysis units D1 and D2, the same analysis items such as AST, ALT, LD, ALP, TP ALB and the like are set up as their common analysis items they can analyze.

In this case, since these analysis items that are set up for each analysis unit to be used are registered in computer 40, memory 45 thereof functions as a second memory means which stores analysis item information for each analysis unit. Therefore, in the analysis operation, a correspondence is identified between overall analysis items information of the system obtained as a set of all the analysis items assigned for each analysis unit to carry out and the analysis items information of the sample on the sample rack which is read out by the sample ID information reader, then the computer 40 determines a particular analysis unit that can analyze the designated analysis item and at which the sample rack should stopover.

Figure 6:
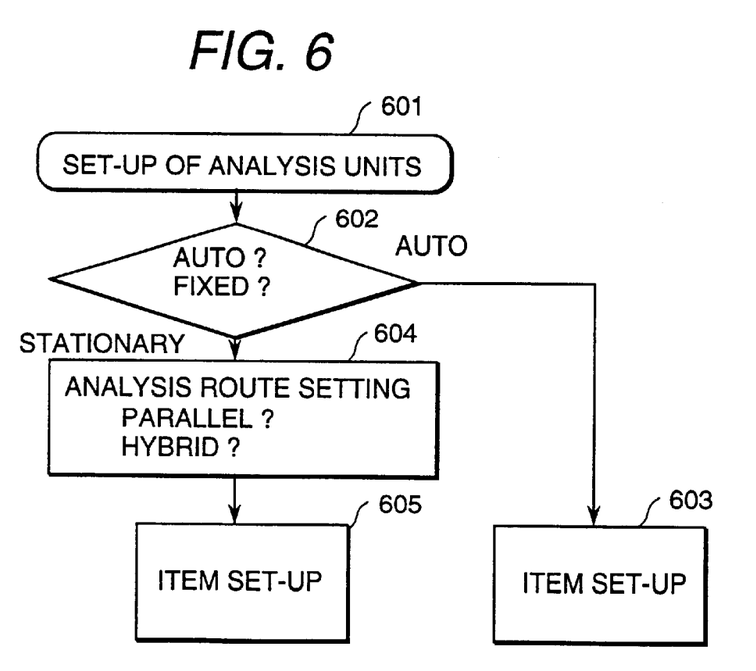
FIG. 6 is a flow chart indicating an example of setting up of system configurations for the sample analysis system of the invention.

On the other hand, when the "stationary" is designated in step 602 in FIG. 6, then in step 604, it is set up whether its analysis route is a parallel type or hybrid type. Then, in step 605, analysis items are set up for each analysis unit in the same manner as in step 603.

When setting up a combination of a plurality of analysis units according to each step of FIG. 6, its setup can be executed through monitoring of a setup screen generated by host control computer 40 and displayed on CRT 43 for each step. The generation and display of this setup screen can be realized by any known art.

Figure 7:
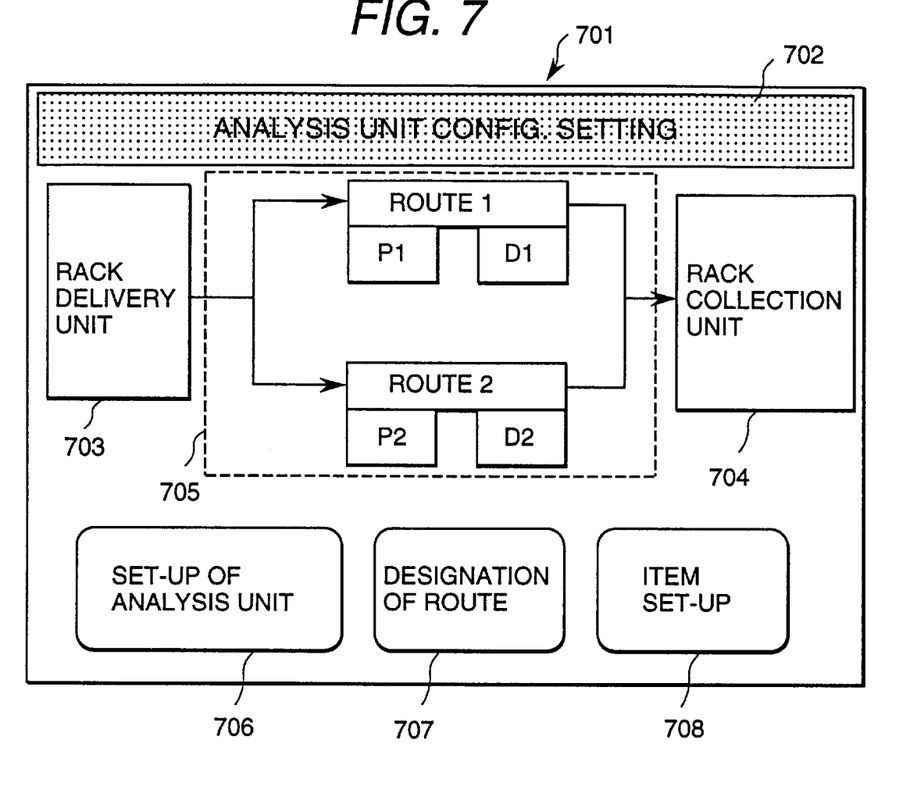
FIG. 7 is a diagram indicating an example of system setup screens displayed while setting up a system configuration.

During setup of a system configuration, when the operator requests the control unit to display an analysis unit setup screen, a system setup screen as indicated in FIG. 7 is displayed on CRT 43. System setup screen 701 in FIG. 7 includes a title block 702, a rack supply display block 703, a rack recovery display block 704, a region 705 encircled by broken line between these two display blocks, an analysis unit setup screen display instruction button 706, an analysis route setup screen display instruction button 707, an item setup screen display instruction button 708, and the like. It should be noted, however, that region 705 encircled by broken line is not displayed in the first stage. When the button of "analysis unit setup" 706 is clicked in this setup screen, a setup screen of FIG. 8 is displayed on CRT 43.

Figure 8:
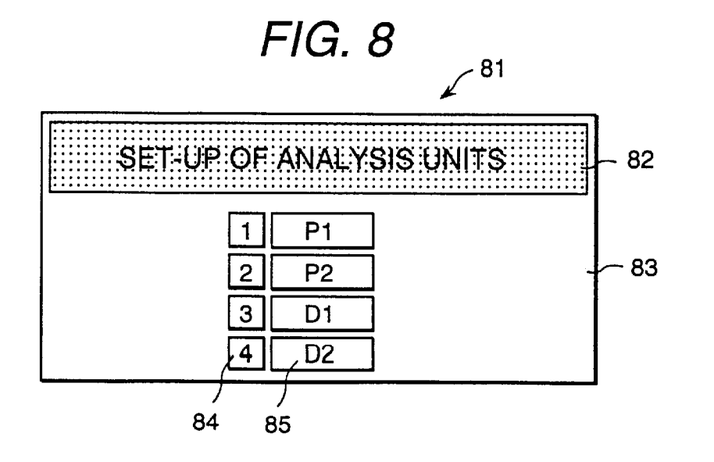
FIG. 8 is a diagram indicating an example of analysis unit setup display screens.

In FIG. 8, analysis unit setup screen 81 includes a title block 82 and an analysis unit display region 83 in which only analysis unit installation position number 84 is displayed initially. When the operator enters the number of an analysis unit to be used and its reagent supply type corresponding to its installation position number into unit input block 85 via operation unit 42, a screen of FIG. 8, for example, is displayed. In this example, "P1" depicts an analysis unit of No. 1 which has a pipetter type reagent supply unit, and "D1" depicts an analysis unit of No. 1 which has a dispenser type reagent supply unit. After completion of entry of all the analysis units to be used, when the end of setup operation is instructed, contents of setup having been made in FIG. 8 are stored in memory 45. In this instance, memory 45 functions as a memory to store information on the combination of the plurality of analysis units having been set up through the screen display means of the invention.

By way of example, screen 81 of FIG. 8 may be displayed as a part of the setup screen of FIG. 7, replaced wholly for the setup screen of FIG. 7, or displayed in a place completely dependent of the setup screen of FIG. 7. Here, setup screen 81 of FIG. 8 is displayed as being replaced by setup screen 701 of FIG. 7. Other setup screens to be described later are displayed in the same manner.

To simplify the description, assume that the combination of analysis units of FIG. 5(B) is designated to be set up. Then, in FIG. 8, numbers 1, 2, 3 and 4 are indicated respectively in analysis unit installation position display blocks 84, and further, symbols P1, P2, D1 and D2 which specify each analysis unit are displayed in unit entry block 85 as shown in FIG. 8. Thereby, an event that at the installation positions 1, 2, 3 and 4, analysis units P1, P2, D1 and D2 are installed respectively in combination, is stored and registered in the memory 45 of the host control computer. This process corresponds to step (601) of FIG. 6.

Upon completion of data entry via setup screen 81 of FIG. 8, when an end key of operation unit 42 is depressed, or a close button (not shown) on screen 81 is clicked, the step returns to the system setup screen of FIG. 7.

Figure 9:
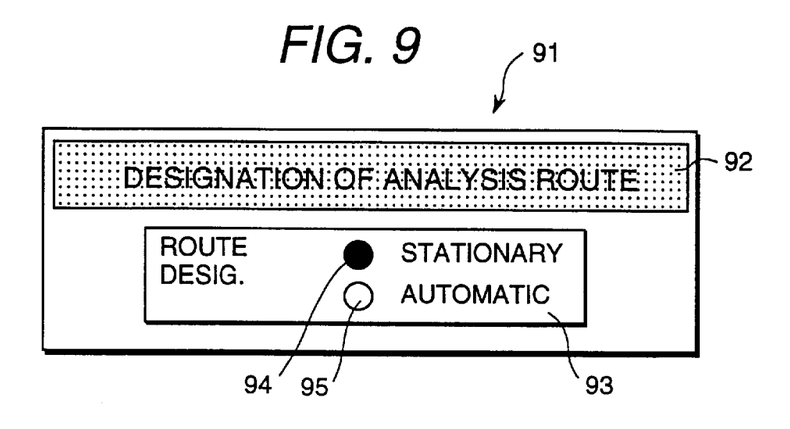
FIG. 9 is an example of analysis route selection display screens.

Then, when button 707 of "analysis route setup" is clicked in FIG. 7, a setup screen of FIG. 9 is displayed. Screen 91 in FIG. 9 which is displayed for selecting a setup method for designating an analysis route includes title block 92 and route designation area 93. In this route designation area 93, buttons 94 and 95 are displayed for selecting either of "stationary" or "automatic". Here, selection of its analysis route whether "stationary" or "automatic" is executed by depressing either one of the buttons. In the case of FIG. 9, the "stationary" analysis route is shown to have been selected. This process corresponds to step 602 in FIG. 6.

Figure 10:
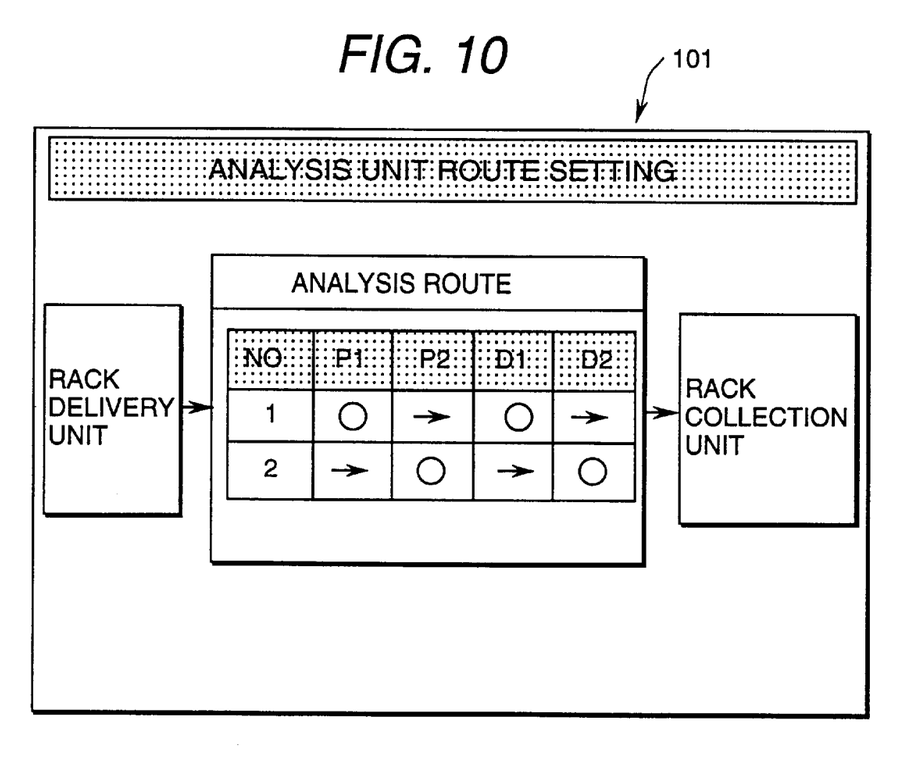
FIG. 10 is an example of analysis unit route designation display screens.

After "stationary" is selected in FIG. 9, if its close button is clicked, a setup screen 101 indicated in FIG. 10 is displayed. Since its analysis route to be designated is the "stationary" analysis route indicated in FIG. 5(B), Nos. 1 and 2 routes are set up. In FIG. 10, in the row of No. 1 corresponding to the first analysis route, analysis units P1 and D1 are designated, and in the row of No. 2 corresponding to the second analysis route, analysis units P2 and D2 are designated. Then, their analysis routes are stored for registration in memory 45 of the host control computer. This step corresponds to step 604 in FIG. 6. After this step, if its close button is clicked, the step returns to the display screen of FIG. 7, having its region 705 changed to have the portion encircled by the broken line.

Figure 11:
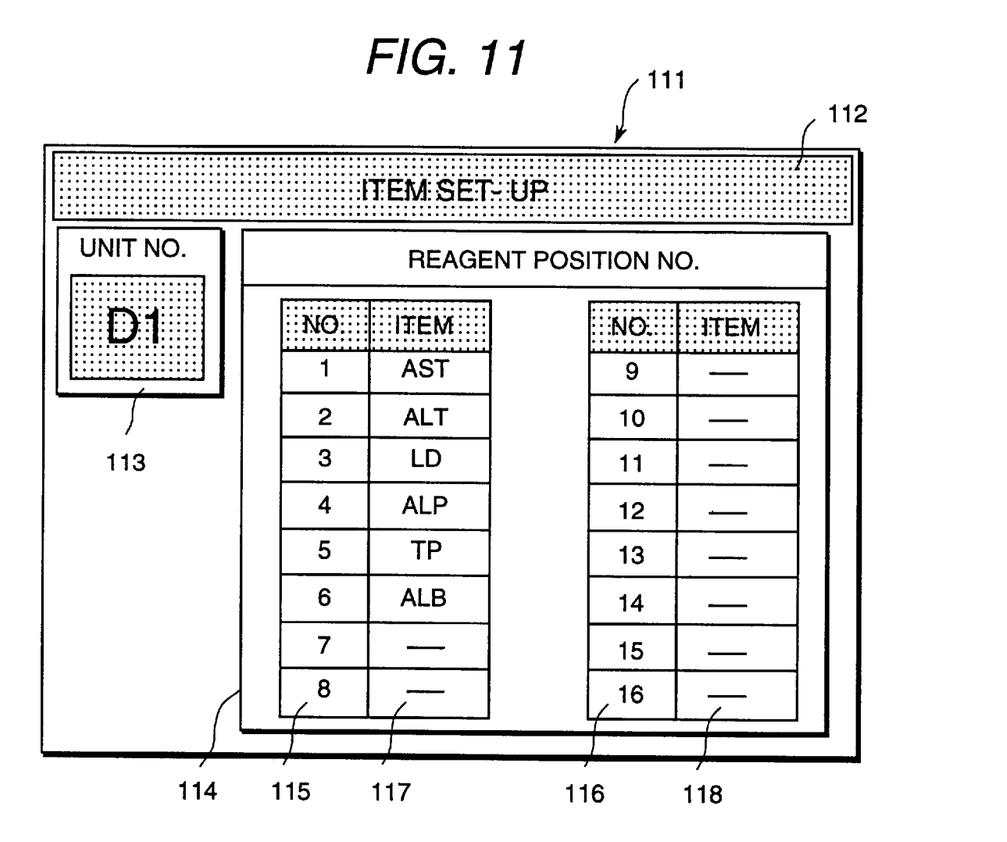
FIG. 11 is an example of analysis items setup display screens of the invention.

In system setup screen 701 of FIG. 7, if "item setup" button 708 is clicked, an analysis item setup screen 111 as indicated in FIG. 11 is displayed. Screen 111 of FIG. 11 has title block 112, analysis unit's name block 113, and display region 114. Then, in display region 114, analysis item setup blocks 117 and 118 are displayed corresponding to reagent position numbers 115, 116. In analysis unit's name block 113, the reagent supply type (P or D) of one of the plurality of analysis units to be used, and its unit number are displayed. Analysis items are set up for each analysis unit. After analysis items for the first analysis unit, for example, P1 have been set up, if its close button is clicked, the second analysis unit, for example, D1 is displayed in analysis unit's name block 113, and its screen is changed to display a setup screen 111 dedicated to D1. After all the setting of analysis items for all the analysis units to be used have been completed, if its close button is clicked, the step returns to setup screen 701 of FIG. 7. FIG. 11 indicates an example of an analysis item setup screen when D1 is designated as an analysis unit. In this case, according to the description of the example of FIG. 6, analysis items of AST, ALT, LD, ALP, TP and ALB are entered respectively to their item boxes corresponding to reagent position numbers 1, 2, 3, 4, 5 and 6 from operation unit 42, and these correlated data are stored in memory 45 for registration. After setup of analysis items for analysis unit D1, when the next analysis unit, for example, P2 is called, "P2" is displayed in analysis unit name box 113, and screen 111 is displayed with empty analysis item setup boxes 117 and 118, which can be filled in the same manner as described above.

In the example of FIG. 5(B), it is assumed that setup conditions for analysis units D1 and D2 are the same. Therefore, for analysis unit D2, the same analysis item is entered into the same analysis item setup box at the same reagent position number as in the analysis unit D1. These data correlated with its reagent supply type and analysis unit number are stored in memory 45. Further, as for analysis units P1 and P2, analysis items of CRU, BUN, CRE and GLU are entered respectively into boxes corresponding to respective reagent position numbers 1, 2, 3 and 4 on their analysis item setup screens, and these correlated data are registered. This step corresponds to steps 603 and 605 in FIG. 6.

After analysis item setup for each analysis unit has been established as one of functional configurations of the sample analysis system, when the operator wishes to know the types of analysis items that have been set up for each analysis unit, the operator can instruct the operation unit 42 to retrieve its stored information on CRT 43 and display all the analysis items corresponding to each analysis unit in a table.

In the case of "automatic", upon determination of a combination of the plurality of analysis units to be used in its sample analysis system, and upon definition of the plurality of analysis items that can be processed by each analysis unit, its analysis system can be said to have been established. Once the functional configuration of such a sample analysis system has been established, since the same configurational conditions can be utilized continuously, all that the operator is required to enter for analysis operation of actual samples is its sample information.

According to the above-mentioned embodiment of the invention, since the positions of its P type analysis unit and its D type analysis unit are interchangeable, flexibility in the system configuration is substantially improved. Further, its system setup can be executed easily by the user through monitoring of its setup screens.

According to the feature of the invention, it becomes possible to change a system configuration for sample processing operation through its system setup screens without changing actual physical arrangements of the plurality of analysis units in the sample analysis system.

What is claimed is:

1. A sample analysis system having a conveyor line for conveying samples, a sample supply unit which accommodates samples to be supplied to the conveyor line, and a plurality of analysis units placed along the conveyor line, comprising:

a display unit displaying a screen including a button calling up an analysis unit setup screen for setting up specific analysis units of the plurality of analysis units to be used and a button calling up an analysis item set up screen for designating specific analysis items, the display unit displaying a set up screen capable of designating analysis items corresponding to the respective analysis units when the analysis unit set up screen is called;

a designating means for designating a combination of the analysis units to be used so as to include at least one analysis unit having a reagent supply unit of a pipetter type and at least one analysis unit having a reagent supply unit of a dispenser type after the setup screen is called up; and a controller controlling operation of the conveyor line so as to convey the samples to the established analysis units.

2. A sample analysis system according to claim 1, which further comprises means for storing combination information of the designated analysis units, the display unit being capable of displaying position information of the designated analysis units and a reagent supply type of each analysis unit.

3. A sample analysis system according to claim 1, further comprising an alarm output means for outputting an alarm when any one of the reagents corresponding to respective analysis items assigned to each analysis unit is not provided in each analysis unit.

* * * * *